(12) United States Patent
Bakhtyari-Nejad-Esfahani

(10) Patent No.: US 8,795,229 B2
(45) Date of Patent: Aug. 5, 2014

(54) INTRAVENOUS NEEDLE INSERTION OR CANNULATION

(75) Inventor: Arash Bakhtyari-Nejad-Esfahani, Nottinghamshire (GB)

(73) Assignee: Olberon Medical Innovation SAS, Loos (FR)

( * ) Notice: Subject to any disclaimer, the term of this patent is extended or adjusted under 35 U.S.C. 154(b) by 0 days.

(21) Appl. No.: 12/302,791

(22) PCT Filed: May 24, 2007

(86) PCT No.: PCT/GB2007/050293
§ 371 (c)(1),
(2), (4) Date: Nov. 26, 2008

(87) PCT Pub. No.: WO2007/138349
PCT Pub. Date: Dec. 6, 2007

(65) Prior Publication Data
US 2009/0198181 A1    Aug. 6, 2009

(30) Foreign Application Priority Data
May 26, 2006   (GB) .................................. 0610553.0

(51) Int. Cl.
*A61M 5/00*   (2006.01)

(52) U.S. Cl.
USPC .......................................... 604/115; 604/116

(58) Field of Classification Search
USPC .............. 604/115, 116, 117; 606/201–204.35
See application file for complete search history.

(56) References Cited

U.S. PATENT DOCUMENTS

| | | | |
|---|---|---|---|
| 2,103,174 A * | 12/1937 | Posada ......................... | 604/115 |
| 2,198,666 A | 4/1940 | Gruskin | |
| 2,457,464 A | 12/1948 | Grose | |
| 3,324,854 A | 6/1967 | Weese | |
| 4,299,219 A * | 11/1981 | Norris, Jr. ..................... | 604/115 |
| 4,314,568 A * | 2/1982 | Loving .......................... | 606/201 |
| 4,332,248 A | 6/1982 | Devitis | |
| 4,393,870 A | 7/1983 | Wagner | |
| 4,576,168 A | 3/1986 | Jalowayski | |
| 4,586,924 A | 5/1986 | Lanning | |
| 4,619,248 A | 10/1986 | Walsh | |
| 4,638,792 A | 1/1987 | Burgin | |
| 4,664,651 A * | 5/1987 | Weinshenker et al. ....... | 604/115 |

(Continued)

FOREIGN PATENT DOCUMENTS

| | | |
|---|---|---|
| DE | 196 20 314 A1 | 11/1997 |
| EP | 1944051 | 7/2008 |
| FR | 542 914 A | 8/1922 |
| FR | 542914 A1 | 8/1922 |

(Continued)

OTHER PUBLICATIONS

Examination Report issued in connection with Russian Application No. 2008151779/14(068052).

*Primary Examiner* — Nicholas Lucchesi
*Assistant Examiner* — Weng Lee
(74) *Attorney, Agent, or Firm* — Knobbe Martens Olson & Bear, LLP

(57) ABSTRACT

A device (10, 110) for facilitating insertion of a needle or a cannula into a vein of a patient, the device (10, 110) comprising means (20, 120, 220) for creating a localized area of reduced pressure at a surface of the patient's skin, so as to facilitate expansion of an underlying part of the vein, and means (26, 226) for enabling insertion of a needle or cannula into the expanded part of the vein.

15 Claims, 6 Drawing Sheets

(56) References Cited

U.S. PATENT DOCUMENTS

| | | | |
|---|---|---|---|
| 5,320,607 A | 6/1994 | Ishibashi | |
| 5,364,362 A | 11/1994 | Schulz | |
| 5,415,647 A * | 5/1995 | Pisarik | 604/115 |
| 5,478,315 A * | 12/1995 | Brothers et al. | 604/115 |
| 5,647,850 A * | 7/1997 | Allen | 604/116 |
| 5,680,872 A | 10/1997 | Sesekura et al. | |
| 5,984,890 A | 11/1999 | Gast et al. | |
| 6,254,580 B1 * | 7/2001 | Svedman | 604/313 |
| 6,394,984 B1 | 5/2002 | Hill | |
| 7,988,667 B2 | 8/2011 | Imai | |
| 2001/0044606 A1 | 11/2001 | Inkpen et al. | |
| 2004/0199140 A1 | 10/2004 | Rue et al. | |
| 2010/0049241 A1 | 2/2010 | Persson | |

FOREIGN PATENT DOCUMENTS

| | | |
|---|---|---|
| FR | 2612401 A | 9/1988 |
| FR | 2612401 A1 | 9/1988 |
| FR | 2698778 A1 | 6/1994 |
| GB | 0553728 A | 3/1946 |
| GB | 2 301 035 A | 11/1996 |
| GB | 2438518 | 11/2007 |
| RU | 2109525 C1 | 4/1998 |
| SU | 1741784 | 6/1992 |
| WO | WO 95/07722 | 3/1995 |
| WO | WO9825512 A1 | 6/1998 |
| WO | WO 01/34019 A | 5/2001 |
| WO | WO02100457 A | 12/2002 |
| WO | WO 2006/007629 | 1/2006 |
| WO | WO 2006/054280 | 5/2006 |

* cited by examiner

INTRAVENOUS NEEDLE INSERTION OR CANNULATION

CROSS REFERENCE TO RELATED APPLICATIONS

This application claims the benefit and priority to and is a U.S. National Phase of PCT International Application Number PCT/GB2007/050293, filed on May 24, 2007. This application claims the benefit and priority to United Kingdom Application No. GB 0610553 filed on May 26, 2006. The disclosures of the above-referenced applications are hereby expressly incorporated by reference in their entirety.

This invention relates to intravenous needle insertion or cannulation, and in particular to a device for facilitating insertion of a needle or cannula into a vein of a patient.

Intravenous cannulation is a commonly used medical technique for withdrawing blood from a patient or for administering medication intravenously. Prior to cannulation of a vein, the vein must be prepared. This preparation involves applying a tourniquet around the part of the patient's body containing the vein, but at a position downstream of the cannulation site. The pressure applied by the tourniquet causes localised expansion of the vein, and hence localised inflation of the vein with venous blood. The cannula can then be inserted into the expanded part of the vein.

Expansion of veins using a tourniquet can sometimes be problematic. The patient may have poor veins due to previous treatments. Alternatively, the patient may be bleeding, and have a low circulating blood volume leading to collapsed veins.

Another problem with the above method of vein expansion is that, for anatomical reasons, use of a tourniquet is only possible with certain veins. For example, the external jugular vein is, in theory, suitable for cannulation due to its superficial nature. However, due to its location in the neck, a tourniquet practically cannot be applied.

Intravenous cannulation can also be particularly difficult in certain situations. For example, where the patient is in a moving ambulance, or where lighting conditions may be less than ideal.

The present invention seeks to address one or more of the above problems.

According to a first aspect of the present invention, there is provided a device for facilitating insertion of a needle or a cannula into a vein of a patient, the device comprising means for creating a localised area of reduced pressure at a surface of the patient's skin, so as to facilitate expansion of an underlying part of the vein, and means for enabling insertion of a needle or cannula into the expanded part of the vein.

The device according to the present invention is advantageous principally because expansion of a part of a vein is facilitated, and hence the device aids insertion of a needle or cannula into the vein. Indeed, sufficient expansion may be achieved without the use of a tourniquet or any other additional medical device. The arrangement of the invention is therefore particularly advantageous in situations where the use of a tourniquet would be difficult or inappropriate.

By "reduced pressure" is meant a pressure that is reduced relative to atmospheric pressure.

The device preferably incorporates a dressing for the patient. The dressing preferably defines a surface of the device that contacts the skin of the patient during use. Most preferably, the dressing is the only part of the device that contacts the patient during use. The dressing is preferably adapted to be attached to the skin of the patient, during use, and preferably therefore includes adhesive on an engagement surface of the dressing. Such attachment assists in retaining the device in place during use, and may also provide a seal for the means for creating a localised area of reduced pressure. One or more release papers preferably cover the adhesive, which are adapted for removal before the dressing is applied to the skin of the patient.

The dressing is preferably adapted to attach the needle or cannula to the skin of the patient, following insertion of the needle or cannula into the vein. The dressing is preferably therefore provided with one or more attachment members that are attachable to both the needle or cannula, and a surrounding part of the patient's skin, most preferably by means of adhesive provided on an engagement surface of the one or more attachment members. The one or more attachment members are preferably adapted to be engaged with the needle or cannula, whilst the device remains engaged with the patient's skin. The one or more attachment members preferably each include a separate release paper, which is removed immediately prior to attachment of the needle or cannula to the patient's skin.

The device may be adapted to remain in place following insertion of the needle or cannula to act as a dressing. However, most preferably, the device comprises a pressure-reduction module and a dressing, the pressure-reduction module being detachable from the dressing. In this arrangement, the pressure-reduction module is preferably detached from the dressing following insertion of the needle or cannula into the vein, such that the dressing remains engaged with the needle or cannula. The pressure-reduction module may be adapted to then be reused with a different dressing, following sterilisation, or most preferably the pressure-reduction module is adapted to be disposable following detachment from the dressing.

The device preferably includes means for detaching the pressure-reduction module from the dressing. Such detachment means may include a removable ribbon or strip attached to a weakened portion of the dressing, such that removal of the ribbon or strip removes the weakened part of the dressing, thereby separating the dressing from the pressure-reduction module. Other possibilities include perforations formed in the dressing, a removable adhesive ribbon or strip that connects the pressure-reduction module and the dressing together, a sufficiently weak adhesive directly connecting the pressure-reduction module and the dressing together, or a combination of these arrangements.

The device may include means for equalising the localised area of reduced pressure with atmospheric pressure, thereby facilitating removal of the device from the patient's skin. For instance, the detachment means may be adapted to equalise the localised area of reduced pressure with atmospheric pressure. The means for creating a localised area of reduced pressure may include a fluid chamber, the interior of which has a reduced pressure, and in this case a removable ribbon or strip of the detachment means is preferably adapted to enable ambient air to flow into the fluid chamber on removal of the ribbon or strip. For example, the ribbon or strip may occlude one or more openings in a wall of the fluid chamber, which are opened on removal of the ribbon or strip.

The surface of the device that engages the skin of the patient is preferably adapted to substantially match the contours of the part of the patient's skin with which the device is to be engaged. In particular, where the device is intended for engagement with the skin of a patient's limb, such as an arm, the engagement surface preferably has an arched cross-sectional shape.

The means for creating an area of reduced pressure adjacent to a surface of the skin preferably includes a fluid chamber provided with an outlet, whereby expulsion of fluid from the fluid chamber through the outlet results in the creation of an area of reduced pressure at a surface of the patient's skin. The fluid will typically be air. However, the use of alternative fluids such as liquid, or a gel may be envisaged. The base of the fluid chamber may be defined by a surface of the skin to which the device has been applied and/or the dressing attached to the patient's skin. For instance, the dressing may include an opening, such that a peripheral part of the base of the chamber is defined by the dressing, and the remainder of the base of the chamber is defined by the patient's skin.

The outlet is preferably arranged so as not to allow fluid to enter the fluid chamber. This arrangement enables the pressure within the fluid chamber to be maintained, so that the localised area of reduced pressure is maintained. Most preferably, the outlet has the form of a one-way valve, which may have the form of an umbrella valve, a duck-billed valve, or any other suitable valve. Furthermore, the one-way valve may be a separate component, or may be integrally formed in the wall of the fluid chamber.

The means for expelling fluid from the fluid chamber may take the form of a resiliently deformable fluid chamber, which is adapted to be collapsed by a user so as to expel fluid through the outlet. In this embodiment, the resilient nature of the enclosure causes elastic energy to be stored within the material of the enclosure during its collapse, and atomic forces within that material act to reform the enclosure towards its original configuration. As the enclosure reforms towards its original configuration, air is prevented from entering the air chamber from the surroundings, and hence the pressure within the air chamber is reduced relative to atmospheric pressure. The enclosure will continue to reform back to its original shape until the atomic forces causing this reformation are balanced by the difference between the pressure within the air chamber and atmospheric pressure. This arrangement may be of simple construction, and hence have reduced manufacturing costs relative to alternative methods.

Alternatively, other means of expelling fluid from the fluid chamber may be envisaged, such as a syringe or a vacuum pump. Indeed, a combination of such means could be incorporated into the device. For example, the device may include a resiliently deformable fluid chamber, an outlet with a one-way valve, and means for connecting a syringe, a vacuum pump or other suction device to the one-way valve to further expel fluid from the fluid chamber.

The device is preferably adapted for use with a needle or cannula that is independent from the device, and most preferably a separate component from the device. In this arrangement, the device may be of very simple construction, with consequently reduced manufacturing costs.

The device preferably includes a first end that is adapted to apply more pressure to the skin of a patient than the pressure applied by a second end of the device, where the first end is adapted to be located, in use, downstream relative to the second end, with reference to blood flow within the vein. The first end may have a contact surface of reduced area relative to the contact surface of the second end. In particular, the first end may include a projection for engaging the skin of the patient with a reduced contact surface, for example a projecting rib. Alternatively, or in addition, the first and second ends may have a different flexibility, and hence a different deformability. For example, the first end may be less flexible, and hence less deformable, than the second end. In this case, the second end may include a region of reduced thickness relative to the remainder of the device, in order to increase the flexibility of the second end of the device. These arrangements facilitate inflation of the vein, during use, by acting to collapse a part of the vein underlying the first end of the device, whilst allowing expansion of a part of the vein underlying the first end of the device.

The means for allowing insertion of a needle or cannula into an underlying vein may include an access point suitable for enabling a cannula to be inserted into the expanded part of the vein over which the device has been applied. The access point is preferably located at the second end of the device, as discussed above. Provision of an access point enables a needle or cannula to be inserted into an underlying vein without piercing the device. The access point preferably has the form of a cut-away portion of the device, in order to facilitate location of the needle or cannula during use. The access point preferably also enables the needle or cannula to be inclined relative to the surface of the skin during insertion.

According to a further aspect of the invention, there is provided a method of inserting a needle or cannula into a vein, which method comprises the steps of creating a localised area of reduced pressure at a surface of the patient's skin, so as to facilitate expansion of an underlying part of the vein, and inserting a needle or cannula into the expanded part of the vein.

The method according to the invention is preferably performed using the device described above.

Preferred embodiments of the present invention are described below, by way of example only, with reference to the accompanying drawings, in which.

Figure 1:
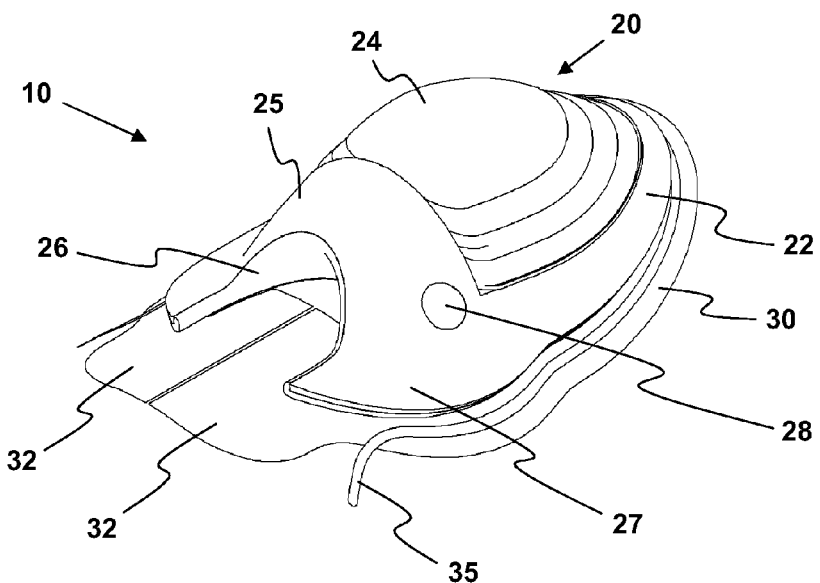
FIG. 1 is a first perspective view of a first embodiment of a device according to the invention.
Figure 2:
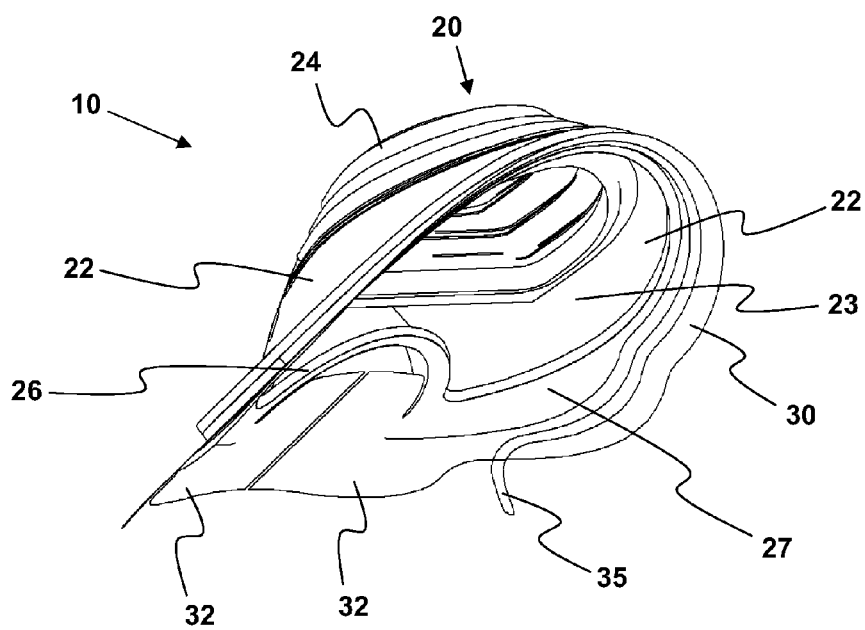
FIG. 2 is a second perspective view of the device of FIG. 1.
Figure 3:
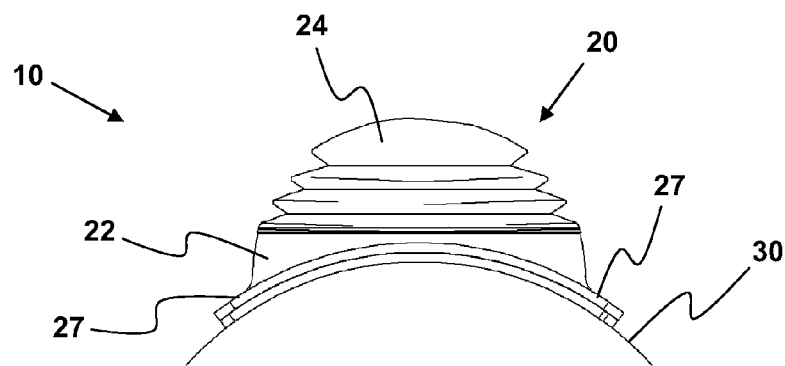
FIG. 3 is a rear view of the device of FIGS. 1 and 2.
Figure 4:
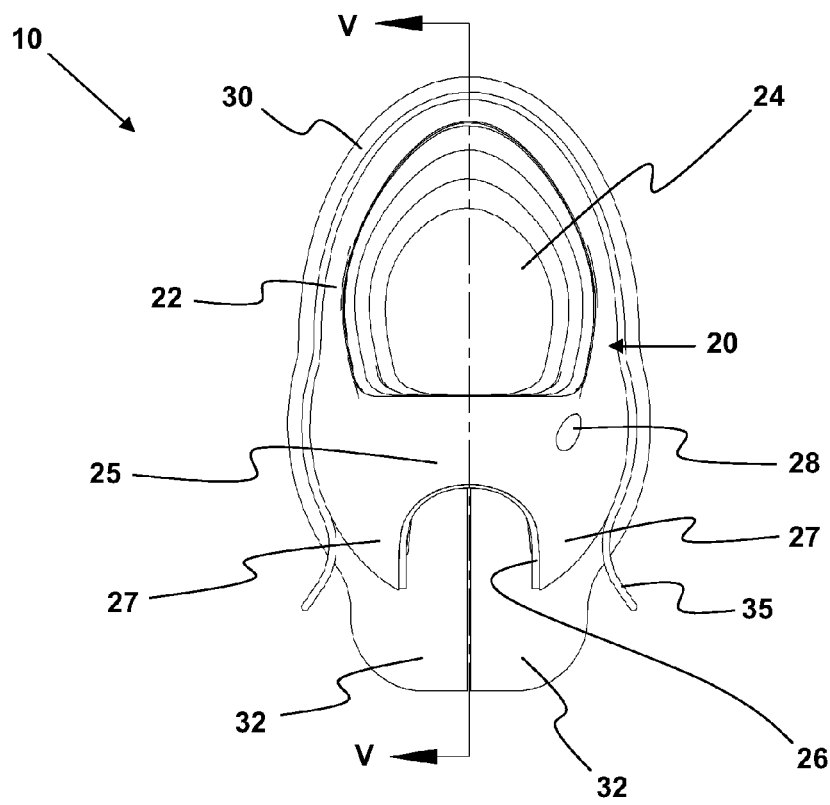
FIG. 4 is a plan view of the device of FIG. 1 to 3.
Figure 5:
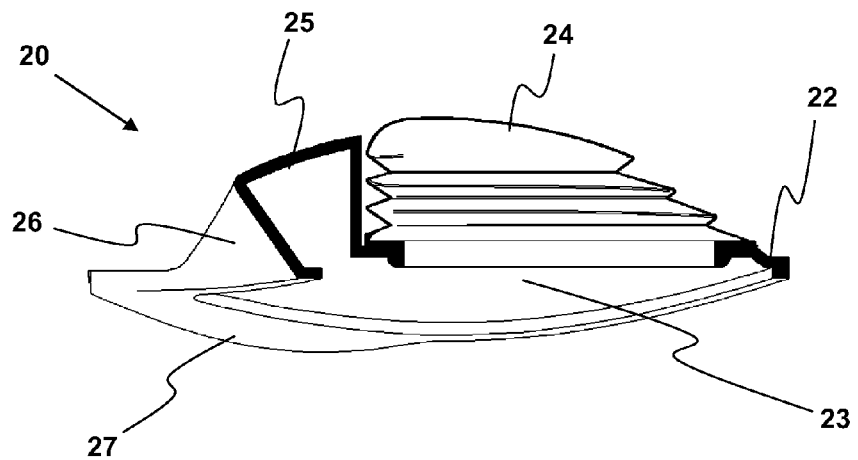
FIG. 5 is a cross-sectional view, along the line V-V in FIG. 4, of a pressure-reduction module 20 that forms part of the device of FIGS. 1 to 4.

FIGS. 1 to 5 show a first embodiment of a device according to the invention, which is generally designated 10. The device 10 comprises a pressure-reduction module 20 and a dressing 30, which are detachable from each other during use, as described in more detail below. The device has a length of approximately 10 to 15 cm, and a width of approximately 2 to 3 cm.

The pressure-reduction module 20 comprises a relatively rigid body 22 and a resiliently deformable enclosure 24 that together define an air chamber 23 having an open lower end. The relatively rigid body 22 is formed of a relatively rigid plastics material, such as polypropylene, and the enclosure is formed of an elastically deformable material, such as a thermoplastic elastomeric material. The relatively rigid housing 22 includes an opening surrounded by a narrow platform to which the resiliently deformable enclosure 24 is bonded, as shown most clearly in FIG. 5. A front portion 25 of the relatively rigid body 22 is also provided that defines part of the air chamber 23. The remainder of the air chamber 23 is defined by a side wall of the relatively rigid body 22 and the resiliently deformable enclosure 24.

The relatively rigid body 22 also includes a peripheral flange 27 that is more flexible than the remainder of the relatively rigid body 22, and hence facilitates formation of a seal between the device 10 and the surface of the patient's skin. This flange 27 has a slightly arched cross-sectional shape and a reduced thickness relative to the remainder of the relatively rigid body 22.

The enclosure 24 includes a side wall having a plurality of folds, in a concertina-like arrangement, that enable the enclosure 24 to be resiliently collapsed, thereby reducing the volume of the air chamber 23. In particular, the enclosure 24 is adapted such that manual pressure applied by a user to an upper surface of the enclosure 24, in the general direction of the patient's skin, will collapse the enclosure 24. The air chamber 23 is substantially air-tight, save for a one-way valve 28 formed in the front portion 25 of the relatively rigid body 22. The one-way valve 28 enables air to exit the air chamber 23, during collapse of the enclosure 24, but prevents air entering the air chamber 23.

The resilient nature of the enclosure 24 causes elastic energy to be stored within the material of the enclosure 24 during its collapse, and following release of manual pressure from the enclosure 24, atomic forces within that material act to reform the enclosure 24 towards its original configuration. As the enclosure 24 reforms towards its original configuration and hence the volume of the air chamber 23 increases, air is prevented from entering the air chamber 23 from the surroundings, and hence the pressure within the air chamber 23 is reduced relative to atmospheric pressure. The enclosure 24 will continue to reform back to its original shape until the atomic forces causing this reformation are balanced by the difference between the pressure within the air chamber 23 and atmospheric pressure. An area of reduced pressure is therefore formed across the surface of the skin that underlies the air chamber 23.

A rear end of the relatively rigid body 22 has a reduced width relative to the front portion 25, and is rounded in form. The rear end of the relatively rigid body 22 is intended to be the end of the device 10 that would be situated downstream of the intended cannulation site, and hence the end of the device 10 that would point towards the heart of the patient. In this arrangement, manual application of pressure by a user at the rear end of the device 10 will act to collapse the vein at that point, and hence facilitate expansion of the vein at the front portion 25 and the site of cannulation. The rear end of the relatively rigid body 22 is therefore sufficiently rigid to enable this collapse of the underlying part of the vein on application of pressure by a user.

The front portion 25 of the relatively rigid body 22 is intended to be the end of the device 10 that would be positioned furthest from the patient's heart and approximately at the site of cannulation. In particular, the front portion 25 includes a horseshoe-shaped cut-away portion 26, which defines a site of cannulation on the surface of the patient's skin, and hence facilitates location of the cannula at an appropriate area of the skin for insertion into an enlarged part of the vein underlying the device 10. In particular, the cannula may be inserted at an angle to the surface of the skin, so that the cannula is inserted into the portion of the vein that is situated directly underneath the device 10.

Furthermore, the front portion of the relatively rigid body 22 has an enlarged flange 27 relative to the flange 27 at the rear end of the relatively rigid body 22, so that less pressure is applied by the device 10 to the patient's skin at the front end of the device 10 than at the rear end of the device 10. This arrangement facilitates expansion of the vein in the region of the cannulation site.

The dressing 30 is detachably fixed to the lower surface of the flange 27 of the pressure-reduction module 20, and also extends outwardly a substantially constant distance beyond the perimeter of the flange 27. The dressing 30 does not, therefore, extend across the lower end of the air chamber 23, so that the base of the air chamber 23 is defined in use by the patient's skin. In addition, the dressing 30 includes a pair of generally rectangular wings 32 that extend from each side of the cut-away portion 26. The wings 32 extend across a front part of the cut-away portion 26, but they are separated along the longitudinal axis of the device 10. The wings 32 also extend a short distance beyond the front end of the pressure-reduction module 20. The wings 32 are adapted to be folded over the side walls of the cut-away portion 26 during insertion of the cannula, and then engaged with exposed surfaces of corresponding wings of the cannula and surrounding areas of the patient's skin, thereby securing the cannula to the patient's skin.

The dressing 30 includes an engagement surface intended for application to the patient's skin, and this engagement surface is provided with a layer of adhesive for attaching the device 10 to the patient's skin. The presence of the layer of adhesive ensures good adherence of the device 10 to the patient's skin, and hence ensures that the air chamber 23 is substantially air-tight during use. The adhesive is preferably of a type that allows simple and pain-free removal of the dressing 30 in due course, but which also ensures good adhesion of the dressing 30 to the skin when in use. Suitable adhesives are well known to those skilled in the art. A release paper covers the adhesive on the engagement surface of the dressing 30, until it is removed immediately prior to application of the device 10 to the patient's skin. In addition, the wings 32 of the dressing 30 each include a separate release paper that covers the adhesive that would otherwise be exposed when the wings 32 are folded over the side walls of the cut-away portion 26 during insertion of the cannula. These release papers are removed prior to engagement of the wings 32 of the dressing 30 with the wings of the cannula and the surrounding areas of the patient's skin.

In order to detach the pressure-reduction module 20 from the dressing 30 following cannulation, the device 10 is provided with a release ribbon 35 that is attached to a weakened part of the dressing 30 that extends about the perimeter of the flange 27 of the pressure-reduction module 20. The ribbon 35 is adapted so that peeling the ribbon 35 from one end detaches the part of the dressing 30 attached to the flange 27 from the remainder of the dressing 30, so that the pressure reduction module 20 also becomes detached from the remainder of the dressing 30. Perforations are also provided in the dressing 30 between the wings 32 and the pressure-reduction module 20, in order that the pressure reduction module 20 may also be detached from the wings 32 of the dressing 30.

In use, the device 10 is placed on a suitably prepared area of a patient's skin over the vein into which the cannula is to be inserted, with the longitudinal axis of the device 10 aligned along the longitudinal axis of the vein. The front portion 25 of the pressure-reduction module 20 is located with the site of cannulation disposed within the cut-away portion of the pressure-reduction module 20, and the rear end of the pressure-reduction module 20 is located downstream of the front portion 25. The engagement surface of the dressing 30 is fastened to the patient's skin by means of the layer of adhesive, following removal of the principal release paper.

Pressure is applied by the user to the rear end of the device 10, towards the patient's skin, in order to collapse the underlying part of the vein and hence facilitate expansion of the part of the vein that underlies the air chamber 23. The enclosure 24 of the pressure-reduction module 20 is at this stage in its non-deformed configuration, and hence the air chamber 18 is charged with a volume of air. A portion of that volume of air is then removed from the air chamber 23 by the application of thumb or finger pressure to the upper surface of the enclosure 24, such that the enclosure 24 is collapsed and the volume of the air chamber 23 is reduced. A portion of the air within the air chamber 23 therefore exits the air chamber 18 via the one-way valve 28. When pressure is released by the user from the enclosure 24, the enclosure 24 will reform towards its non-deformed configuration and hence the volume of the air chamber 23 will increase.

This action reduces the pressure within the air chamber 23 relative to atmospheric pressure, and hence reduces the pressure acting upon the area of skin underlying the air chamber 23 of the device 10. A localised region of reduced pressure is therefore formed over the vein, which causes the part of the vein underlying the air chamber 23 to expand.

The cannula is then inserted into the skin at the site of cannulation defined by the cut-away portion 26 of the device 10, with the cannula inclined relative to the skin so that the cannula extends into the expanded part of the vein that underlies the air chamber 23 of the device 10. The cannula is then secured to the patient's skin by the wings 32 of the dressing 30, following removal of the release papers of those wings 32. In particular, the wings 32 of the dressing 30 will typically secure corresponding wings of the cannula to the patient's skin. The wings 32 of the dressing 30 may folded upwards by the user before, and also during, insertion of the cannula, so that the wings 32 of the dressing 30 are situated above the corresponding wings of the cannula after insertion, and hence engagement of the wings 32 of the dressing 30 with the cannula is facilitated.

Once the cannula 38 has been secured to the patient's skin, the release ribbon 35 is removed from the device 10, by peeling from one end, such that the dressing 30 is detached from the pressure-reduction module 20. This action enables ambient air to enter the air chamber 23, and hence equalisation of the pressure within the air chamber 23 with atmospheric pressure. The pressure-reduction module 20 is removed from the patient's skin and is then suitable for disposal as waste. The dressing 30, however, remains attached to the patient's skin in order to maintain the cannula in place, until the cannula is removed.

The device 10 provides a simple solution to the problem of expanding part of a vein for cannulation and venipuncture where there are anatomical or situational difficulties. For example, it is useful in vein preparation for blood sampling and blood donation where a patient has comparatively difficult or awkward veins for needle or cannula insertion. It also provides a simple way of preparing a vein for cannulation, which can be useful where conditions are less than ideal. The device may also be used with a tourniquet in certain circumstances to augment and optimise vein preparation.

Figure 6:
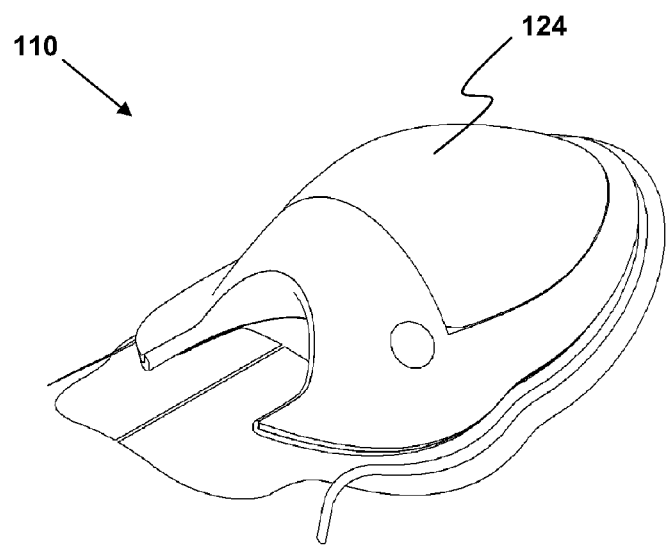
FIG. 6 is a perspective view of a second embodiment of a device according to the invention.
Figure 7:
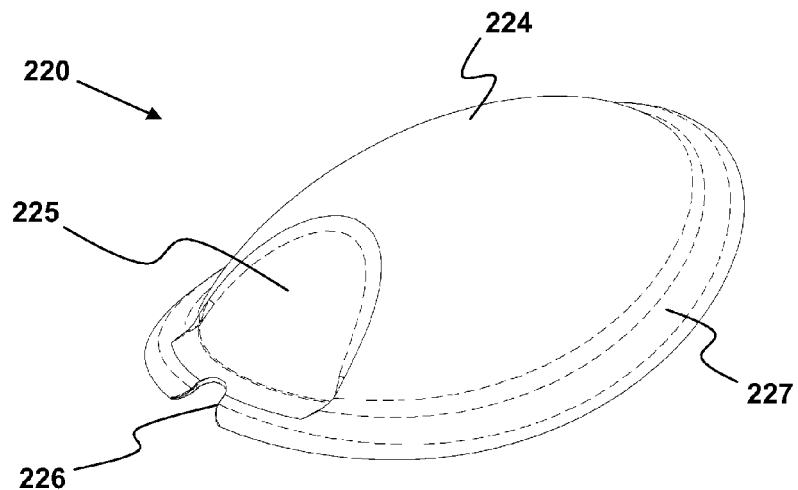
FIG. 7 is a first perspective view of a third embodiment of a device according to the invention.
Figure 8:
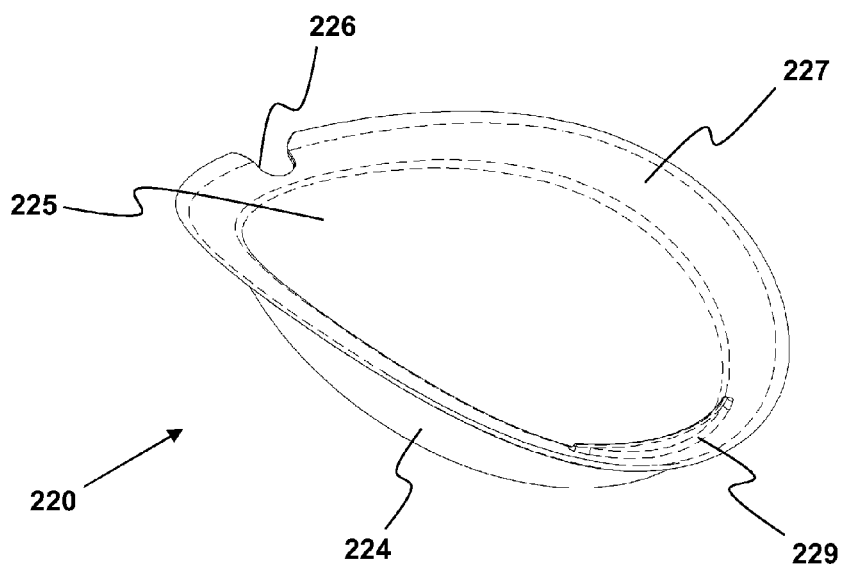
FIG. 8 is a second perspective view of the device of FIG. 7.
Figure 9:
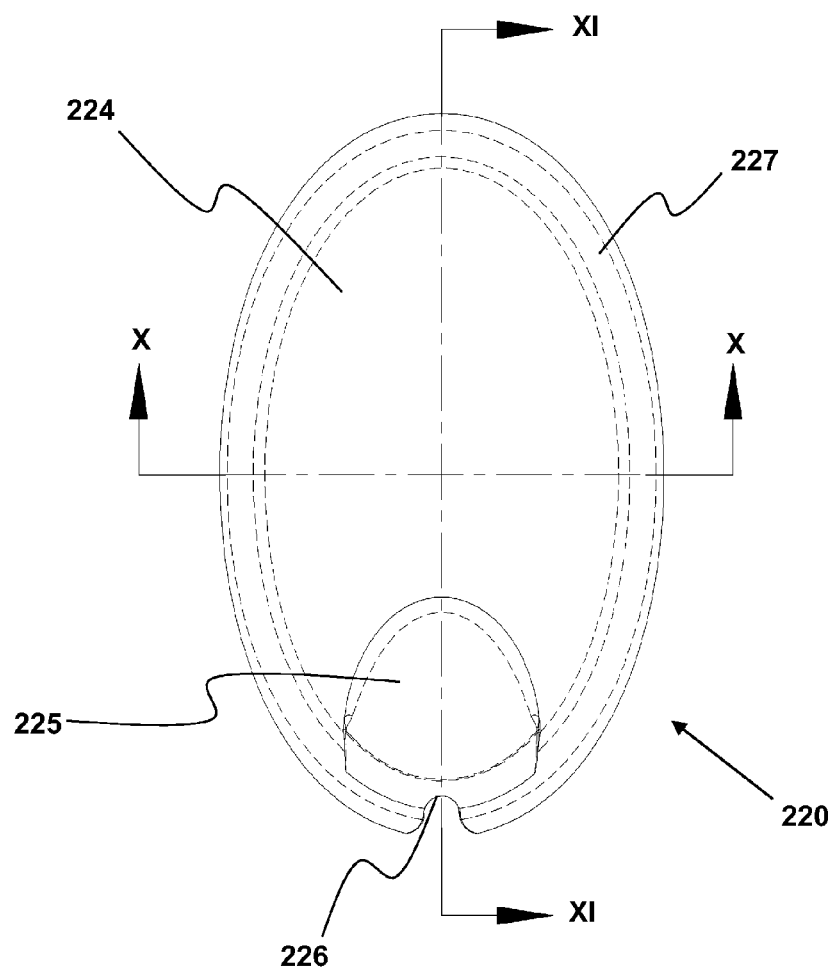
FIG. 9 is a plan view of the device of FIGS. 7 and 8.
Figure 10:
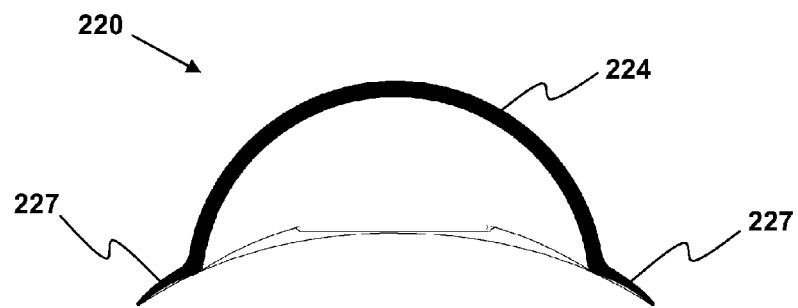
FIG. 10 is a cross-sectional view, along the line X-X in FIG. 9, of the device of FIGS. 7 to 9.
Figure 11:
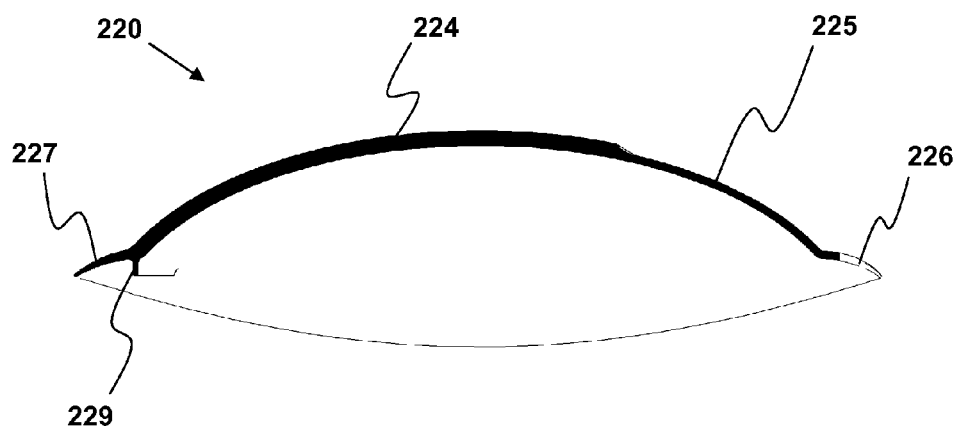
FIG. 11 is a cross-sectional view, along the line XI-XI in FIG. 10, of the device of FIGS. 7 to 10.

FIG. 6 shows a second embodiment of a device according to the invention, which is generally designated 110. This embodiment of the device 110 is identical to the first embodiment 10, save that the resiliently deformable enclosure 124 does not include a folded sidewall. Instead, the enclosure 24 is formed of a sufficiently elastic material that a similar collapse of the enclosure 124 is achievable, during use. Furthermore, the enclosure 24 is formed with a shape and configuration in which the atomic forces within the material of the collapsed enclosure 24 act to reform the enclosure 24 towards its original configuration.

FIGS. 7 to 11 show a pressure-reduction module 220 of a third embodiment of a device according to the invention. The pressure-reduction module 220 is formed as a single component of an elastically deformable material by injection moulding. The pressure-reduction module 220 comprises a resiliently deformable enclosure 224, having the form of a slightly elongated dome, and a peripheral flange 227. The flange 227 is more flexible than the remainder of the enclosure 224, and hence facilitates formation of a seal between the pressure-reduction module 220 and the surface of the patient's skin. The flange 227 has a slightly arched cross-sectional shape and a reduced thickness relative to the remainder of the enclosure 224.

A rear end of the pressure-reduction module 220 is intended to be the end of the device 10 that would be situated downstream of the intended cannulation site, and hence the end of the pressure-reduction module 220 that would point towards the heart of the patient. In this arrangement, manual application of pressure by a user at the rear end of the pressure-reduction module 220 will act to collapse the vein at that point, and hence facilitate expansion of the vein at the front portion 225 and the site of cannulation. The rear end of the pressure-reduction module 220 is therefore sufficiently rigid to enable this collapse of the underlying part of the vein on application of pressure by a user. In order to facilitate collapse of the underlying part of the vein, the rear end of the pressure-reduction module 220 is provided with a projecting rib 229 at the interior edge of the flange 227, which increases the pressure applied to the skin of the patient at the rear end of the pressure-reduction module 220.

The pressure-reduction module 220 also includes a front portion 225 that is intended to be the end of the pressure-reduction module 220 that would be positioned furthest from the patient's heart and approximately at the site of cannulation. In particular, the front portion 225 comprises a region of the enclosure 224 that has a reduced thickness, and hence greater flexibility, than the remainder of the enclosure 224. The greater flexibility of the front portion of the pressure-reduction module 220 reduces the pressure applied to the patient's skin in the proximity of the cannulation site, and hence facilitates expansion of the vein underlying the pressure-reduction module 220. In addition, the front portion 225 of the pressure-reduction module 220 includes a horseshoe-shaped cut-away portion 226 in the flange 227, which defines a site of cannulation on the surface of the patient's skin, and hence facilitates location of the cannula at an appropriate area of the skin for insertion into an enlarged part of the vein underlying the pressure-reduction module 220. In particular, the cannula may be inserted at an angle to the surface of the skin, so that the cannula is inserted into the portion of the vein that is situated directly underneath the device 10.

The third embodiment of a device according to the invention includes the pressure-reduction module 220 of FIGS. 7 to 11, and a dressing (not shown in the Figures) that has a similar form to the dressing 30 of the first embodiment 10. In particular, the dressing of the third embodiment is attached to the flange 227 by a weak adhesive, and includes a pair of wings that project from the front end of the pressure-reduction module 220. The wings of the dressing are adapted to be folded over the front end of the pressure-reduction module 220 during cannulation, and then engaged with the corresponding wings of the cannula to secure those wings to the patient's skin following cannulation. The weak adhesive attaching the dressing to the pressure-reduction module 220 enables the pressure-reduction module 220 to be detached from the dressing following cannulation. In all other respects, the third embodiment functions in an identical manner to the first embodiment 10.

The invention claimed is:

1. A device for facilitating insertion of a needle or a cannula into a vein of a patient, the device comprising a pressure-reduction module adapted to be applied to a surface of the patient's skin and create a localized area of reduced pressure at the surface of the patient's skin over which the pressure-reduction module has been applied, so as to facilitate expansion of an underlying part of the vein, wherein the pressure reduction module has the form of an enclosure having a peripheral flange and the device incorporates a dressing for the patient, the dressing being located against the flange and defining a surface of the device that contacts the skin of the patient during creation of the localized area of reduced pressure, and the device is arranged to enable insertion of a needle or cannula into the expanded part of the vein, whilst the pressure-reduction module remains applied to the surface of the patient's skin.

2. A device as claimed in claim 1, wherein the dressing is adapted to attach the needle or cannula to the skin of the patient, following insertion of the needle or cannula into the vein.

3. A device as claimed in claim 1, wherein the device is adapted to remain in place following insertion of the needle or cannula to act as a dressing.

4. A device as claimed in claim 1, wherein the pressure-reduction module is detachable from the dressing.

5. A device as claimed in claim 1, wherein the surface of the device that engages the skin of the patient is adapted to substantially match the contours of the part of the patient's skin with which the device is to be engaged.

6. A device as claimed in claim 1, wherein the device includes a fluid chamber provided with an outlet, whereby expulsion of fluid from the fluid chamber through the outlet results in the creation of an area of reduced pressure at a surface of the patient's skin.

7. A device as claimed in claim 6, wherein the device includes a resiliently deformable fluid chamber, which is adapted to be collapsed by a user so as to expel fluid through the outlet.

8. A device as claimed in claim 1, wherein the device comprises a resiliently deformable enclosure having the form of a dome.

9. A device as claimed in claim 1, wherein the device includes an access point suitable for enabling a cannula to be inserted into the expanded part of the vein over which the device has been applied, and the device including a first end that is adapted to apply more pressure to the skin of a patient than the pressure applied by a second end of the device, where the first end is adapted to be located, in use, downstream relative to the second end, with reference to blood flow within the vein, and the access point is located at the second end of the device.

10. A device as claimed in claim 9, wherein the first end includes a projection for engaging the skin of the patient with a reduced contact surface.

11. A device as claimed in claim 9, wherein the second end includes a region of reduced thickness relative to the remainder of the device, in order to increase the flexibility of the second end of the device.

12. A device as claimed in claim 9, wherein the access point has the form of a cut-away portion of the device, in order to facilitate location of the needle or cannula during use.

13. A device as claimed in claim 12, wherein the access point enables the needle or cannula to be inclined relative to the surface of the skin during insertion.

14. A method of inserting a needle or cannula into a vein, which method comprises the steps of creating a localized area of reduced pressure at a surface of the patient's skin, so as to facilitate expansion of an underlying part of the vein, and inserting a needle or cannula into the expanded part of the vein, wherein the method is performed using a device as defined by claim 1.

15. A device for facilitating insertion of a needle or a cannula into a vein of a patient, the device comprising a pressure-reduction module, the pressure-reduction module being a resiliently deformable enclosure having the form of a dome, and a peripheral flange adapted to be applied to a surface of the patient's skin, the dome being adapted to collapse by the application of thumb or finger pressure thereto by a user and thereby expel fluid therefrom such that the resilience of the deformable enclosure creates a localized area of reduced pressure at the surface of the patient's skin over which the pressure-reduction module has been applied, so as to facilitate expansion of an underlying part of the vein, wherein the device is arranged to enable insertion of a needle or cannula into the expanded part of the vein, whilst the pressure-reduction module remains applied to the surface of the patient's skin.

* * * * *